United States Patent
Kawanishi et al.

(10) Patent No.: US 7,795,471 B2
(45) Date of Patent: Sep. 14, 2010

(54) PROCESS FOR TRANS-4-AMINO-1-CYCLOHEXANECARBOXYLIC ACID DERIVATIVES

(75) Inventors: Yasuyuki Kawanishi, Amagasaki (JP); Masaaki Uenaka, Amagasaki (JP); Munenori Matsuura, Amagasaki (JP)

(73) Assignee: Shionogi & Co., Ltd., Osaka-Shi (JP)

( * ) Notice: Subject to any disclaimer, the term of this patent is extended or adjusted under 35 U.S.C. 154(b) by 0 days.

(21) Appl. No.: 12/464,031

(22) Filed: May 11, 2009

(65) Prior Publication Data

US 2009/0221817 A1 Sep. 3, 2009

Related U.S. Application Data

(62) Division of application No. 12/247,057, filed on Oct. 7, 2008, now Pat. No. 7,547,800, which is a division of application No. 11/871,851, filed on Oct. 12, 2007, now Pat. No. 7,459,580, which is a division of application No. 10/505,963, filed as application No. PCT/JP03/02729 on Mar. 7, 2003, now Pat. No. 7,314,950.

(30) Foreign Application Priority Data

Mar. 12, 2002 (JP) ............... 2002-067548

(51) Int. Cl.
*C07D 265/30* (2006.01)
*C07C 205/00* (2006.01)
*C07C 231/00* (2006.01)

(52) U.S. Cl. .................. 564/80; 560/125; 562/507; 568/30; 568/31

(58) Field of Classification Search ............ 560/125; 564/80
See application file for complete search history.

(56) References Cited

U.S. PATENT DOCUMENTS

| | | | |
|---|---|---|---|
| 5,418,233 A | 5/1995 | Linz et al. | |
| 5,700,801 A | 12/1997 | Pieper et al. | |

FOREIGN PATENT DOCUMENTS

| | | |
|---|---|---|
| EP | 537696 A1 | 4/1993 |
| EP | 718287 A2 | 6/1996 |
| WO | WO 97/15567 | 5/1997 |
| WO | WO 01/37826 A1 | 5/2001 |

OTHER PUBLICATIONS

Greene, Theodora W., Protective Groups in Organic Synthesis Third Edition, John Wiley & Sons, Inc., 1999, pp. 586 to 589.
Palaima, A.I., et al., Bulletin of the Academy of Sciences of the USSR, Division of Chemical Science, vol. 26, No. 1, (Jul. 20, 2977).

*Primary Examiner*—Sikarl A Witherspoon
(74) *Attorney, Agent, or Firm*—Birch, Stewart, Kolasch & Birch, LLP

(57) ABSTRACT

The present invention relates to a process for preparing a compound of the formula:

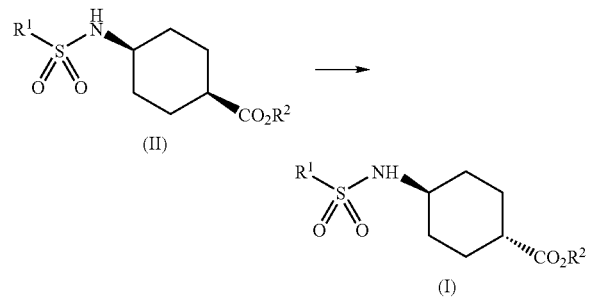

wherein $R^1$ is lower alkyl, $R^4$ is hydrogen or lower alkyl, and Z is optionally substituted lower alkyl, optionally substituted lower alkenly, optionally substituted amino, optionally substituted lower alkoxy, optionally substituted carbocyclyl or optionally substituted heterocyclyl.

10 Claims, No Drawings

PROCESS FOR TRANS-4-AMINO-1-CYCLOHEXANECARBOXYLIC ACID DERIVATIVES

This application is a Divisional of application Ser. No 12/247,057 filed Oct. 7, 2008, which in turn is a Divisional of application Ser. No. 11/871,851 filed on Oct. 12, 2007 which issued as U.S. Pat. No. 7,459,580, which in turn is a Divisional of U.S. application Ser. No. 10/505,963 filed on Oct. 21, 2004 which issued as U.S. Pat. No. 7,314,950. Priority of the above applications is claimed under 35 U.S.C. §120. U.S. application Ser. No. 10/505,963 is the national phase of PCT International Application No. PCT/JP2003/002729 filed on Mar. 7, 2003 under 35 U.S.C. §371. This Application also claims priority to Application No. JP 2002-067548 filed in Japan on Mar. 12, 2002 under 35 U.S.C. §119.

TECHNICAL FIELD

The present invention relates to a process for the preparation of trans-4-amino-1-cyclohexanecarboxilic acid derivatives which are useful as intermediates of medicaments such as NPYY5 receptor antagonists and the like.

BACKGROUND ART

Trans-4-amino-1-cyclohexanecarboxilic acid derivatives are useful as intermediates of medicament etc. For example, trans-4-(2-methylpropane-2-sulfonylamino)cyclohexanecarboxylic acid and the like are disclosed as intermediates of NPYY5 receptor antagonists in the following Patent Literature 1. However, an isolation yield of the trans isomer is only 40% by the process described in the literature because the cis isomer does not smoothly isomerize to the trans isomer even if it is reacted for many hours. Therefore, the process is not necessarily satisfying as a process for a mass-production of the trans isomer.

A development of a convenient process for the preparation of trans-4-amino-1-cyclohexanecarboxylic acid has been desired in order to efficiently mass-produce various trans isomers of amino derivatives and/or carboxyl derivatives from 4-amino-1-cyclohexane carboxylic acid.

Patent Literature WO01/37826

DISCLOSURE OF INVENTION

An object of the present invention is to provide an efficient process for the preparation of trans-4-amino-1-cyclohexanecarboxylic acid derivatives.

BEST MODE FOR CARRYING OUT THE INVENTION

As a result of various studies of an isomerization of cis-4-amino-1-cyclohexanecarboxylic acid to the trans isomer, the inventors of the present invention found that the isomerization rate and isolation yield are remarkably increased by using a specific solvent or crystallization solvent, or introducing a specific substituent on an amino group, and the following invention is completed.

(1) A process for the preparation of a compound of the formula:

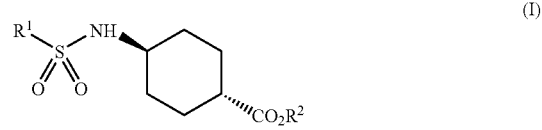

wherein $R^1$ and $R^2$ are each independently lower alkyl, comprising reacting a compound of the formula:

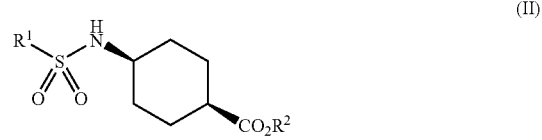

wherein each symbol is the same as defined above, with a base in an aprotic solvent.
(2) The process as described in the above (1) comprising recrystallizing Compound (I) in an aprotic solvent.
(3) The process as described in the above (1) or (2) wherein the aprotic solvent is a nonpolar aprotic solvent.
(4) The process as described in the above (3) wherein the aprotic solvent is toluene.
(5) The process as described in any one of the above (1) to (4) wherein the base is selected from a group of an alkaline metal lower alkoxide, an alkaline metal halide and an alkaline metal amide.
(6) The process as described in the above (5) wherein the base is alkaline metal lower alkoxide.
(7) The process as described in any one of the above (1) to (6) wherein the compound of the formula:

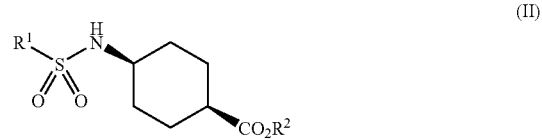

wherein $R^1$ and $R^2$ are each independently lower alkyl, is prepared by reacting a compound of the formula:

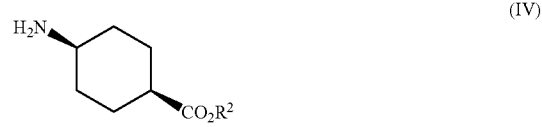

wherein $R^2$ is lower alkyl, with a compound of the formula:

wherein R¹ is lower alkyl to obtain a compound of the formula:

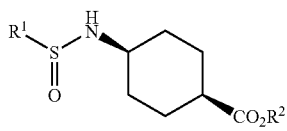
(III)

wherein each symbol is the same as defined above, and by oxidizing Compound (III).

(8) A process for the preparation of a compound of the formula:

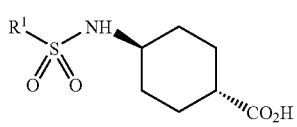
(I')

wherein R¹ is the same as defined above, comprising hydrolyzing Compound (I) obtained by the process as described in any one of the above (1) to (7).

(9) The process as described in the above (8) comprising hydrolyzing Compound (I) which is not isolated from a reaction solution.

(10) The process as described in any one of the above (1) to (9) wherein R¹ is t-butyl and R² is methyl.

(11) A process for the preparation of a compound of the formula:

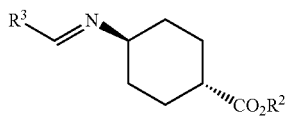
(VIII)

wherein R² is lower alkyl and R³ is optionally substituted phenyl, comprising reacting a compound of the formula:

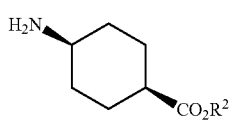
(IV)

wherein R² is the same as defined above with a compound of the formula:

R³—CHO   (VI)

wherein R³ is the same as defined above to obtain a compound of the formula:

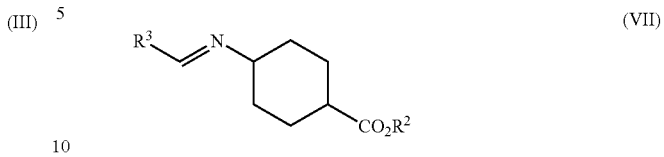
(VII)

wherein each symbol is the same as defined above, and reacting Compound (VII) with a base in an organic solvent.

(12) The process as described in the above (11) wherein R³ is nitrophenyl.

(13) A process for the preparation of a compound of the formula:

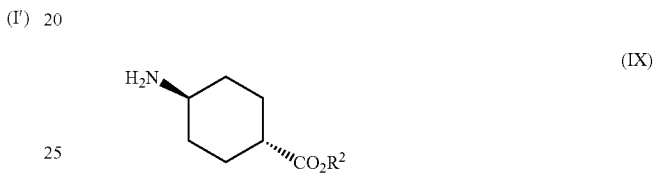
(IX)

wherein R² is the same as defined above, comprising hydrolyzing Compound (VIII) obtained by the process described in the above (11) or (12).

(14) A process for the preparation of a compound of the formula:

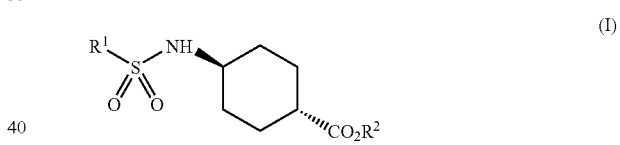
(I)

wherein R¹ and R² are each independently lower alkyl, comprising reacting a compound of the formula:

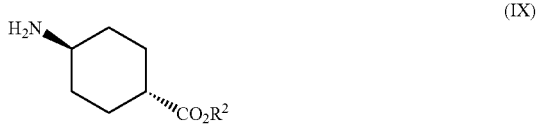
(IX)

wherein R² is the same as defined above, with a compound of the formula:

(V)

wherein R¹ is the same as defined above to obtain a compound of the formula:

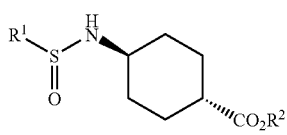

wherein each symbol is the same as defined above, and oxidizing Compound (X).

(15) The process as described in the above (14) wherein Compound (IX) is obtained by the process described in the above (11).

(16) A process for the preparation of a compound of the formula:

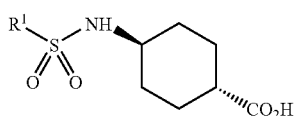

wherein R¹ is lower alkyl, comprising hydrolyzing Compound (I) obtained by the process described in the above (14) or (15).

(17) A compound of the formula:

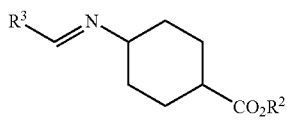

wherein R² is lower alkyl and R³ is optionally substituted phenyl.

(18) A compound of the formula:

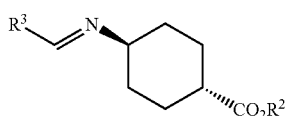

wherein R² is lower alkyl and R³ is optionally substituted phenyl.

(19) A compound of the formula:

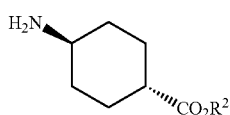

wherein R² is lower alkyl.

(20) A compound of the formula:

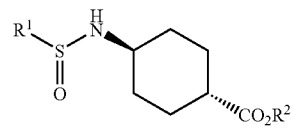

wherein R¹ and R² are each independently lower alkyl.

(21) A process for the preparation of a compound of the formula:

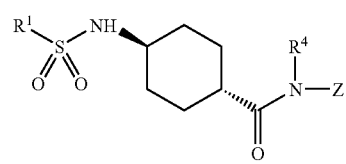

wherein R¹ is lower alkyl, R⁴ is hydrogen or lower alkyl, and Z is optionally substituted lower alkyl, optionally substituted lower alkenyl, optionally substituted amino, optionally substituted lower alkoxy, optionally substituted carbocyclyl or optionally substituted heterocyclyl, prodrug, pharmaceutically acceptable salt or solvate thereof comprising reacting Compound (I') obtained by any one of the processes described in the above (1) to (16) with a compound of the formula:

$$R^4NH—Z \quad (XI)$$

wherein R⁴ and Z are the same as defined above.

The process of the present invention is described in detail below.

(Process 1) Conversion of Compound (II) to Compound (I')

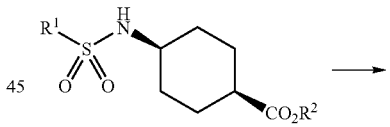

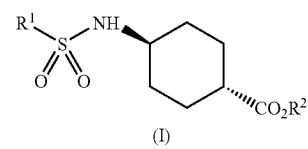

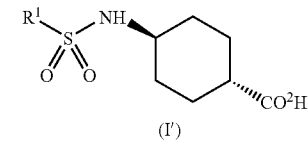

wherein each symbol is the same as defined above.

(Step 1)

Compound (I) can be obtained by reacting cis Compound (II) with a base in a nonpolar aprotic solvent. In the process, cis Compound (II) is isomerized to a trans isomer.

$R^1$ and $R^2$ of Compound (I) are each independently lower alkyl.

Lower alkyl includes a straight or a branched C1 to C6 alkyl and examples are methyl, ethyl, n-propyl, i-propyl, n-butyl, i-butyl, sec-butyl, t-butyl, n-pentyl, i-pentyl, neo-pentyl, tert-pentyl and n-hexyl.

$R^1$ is preferably C3 to C5 alkyl and more preferably t-butyl.

$R^2$ is preferably C1 to C4 alkyl or C1 to C3 alkyl, more preferably methyl or ethyl and most preferably methyl.

The base is not limited as long as it efficiently proceeds to isomerize a cis isomer to a trans isomer, and preferably an alkaline metal lower alkoxide such as sodium methoxide, sodium ethoxide, potassium methoxide, potassium ethoxide and potassium tert-butoxide; an alkaline metal halide such as NaH; and an alkaline metal amide such as lithium diisopropyl amide (LDA), and $NaNH_2$. An alkaline metal lower alkoxide is more preferable and sodium methoxide is most preferable.

The amount of the base is preferably about 1 to 5 mole equivalent and more preferably about 2 to 3 mole equivalent relative to the amount of Compound (II).

The aprotic solvent is not limited as long as it efficiently proceeds to isomerize a cis isomer to a trans isomer, and a nonpolar solvent and a polar solvent are exemplified. Preferable solvent is one in which a trans isomer, i.e. Compound (I) can be more efficiently crystallized after the reaction than a cis isomer, i.e. Compound (II). Examples of an polar aprotic solvent are acetone, tetrahydrofuran and ethyl acetate. Examples of a nonpolar aprotic solvent are aromatic carbohydrates such as benzene, toluene and xylene; aliphatic carbohydrates such as n-hexane; and ethers such as diethyl ether. A nonpolar aprotic solvent is preferable and an aromatic carbohydrate is more preferable and toluene is most preferable.

Reaction temperature is not limited but generally about 50 to 150° C., and preferably about 80 to 110° C.

Reaction time is not limited but generally 1 to 50 hours and preferably about 1 to 3 hours.

The feature of the reaction is to produce trans Compound (I) by isomerizing cis Compound (II). The invention also includes a reaction for isomerizing a cis isomer in a mixture of a cis isomer and a trans isomer to a trans isomer and arising a ratio of the trans isomer in the mixture. The isomerization rate is 90% or more, preferably 95% or more, and most preferably 97 to 100%. The isomerization rate in the specification means the mole ratio of the trans isomer relative to total mole of the cis isomer and the trans isomer after the reaction is completed, and it can be measured by a liquid chromatography or the like.

Compound (I) can be obtained in a high yield by this reaction because cis Compound (II) is efficiently isomerized to a trans isomer and a trans isomer is selectively crystallized.

Compound (I) is preferably recrystallized and examples of a solvent for recrystallization are the same as mentioned above. Even if the aforementioned isomerization rate is less than 100%, trans Compound (I) can be obtained in 100% yield by this recrystallization step.

(Step 2)

Compound (I') can be synthesized by hydrolyzing Compound (I) obtained by the above step.

Examples of a solvent are methanol, ethanol, acetonitrile, toluene and acetone, and methanol is preferable.

Reaction temperature is not limited but generally about 0 to 100° C. and preferably about 0 to 30° C.

Reaction time is not limited but generally about 1 to 50 hours and preferably about 1 to 2 hours.

Examples of a catalyst for this reaction are sodium hydroxide, potassium hydroxide and lithium hydroxide and sodium hydroxide is preferable.

Hydrolysis of Compound (I) can be conducted using Compound (I) which is isolated from the reaction solution obtained by Step 1 or which is not isolated, and preferably conducted using Compound (I) which is not isolated.

When the processes from Compound (II) to Compound (I') are continuously conducted in the same vessel, the yield of Compound (I') can be increased, for example, Compound (I') is obtained from Compound (II) in 90% or more.

Compound (I') is useful as an intermediate of medicaments because it can be utilized as an intermediate of various NPYY5 receptor antagonists by amidation of a carboxyl group.

(Synthesis of Starting Compound (II))

A process for the preparation of Compound (II) is not limited but it can be preferably synthesized in the following method.

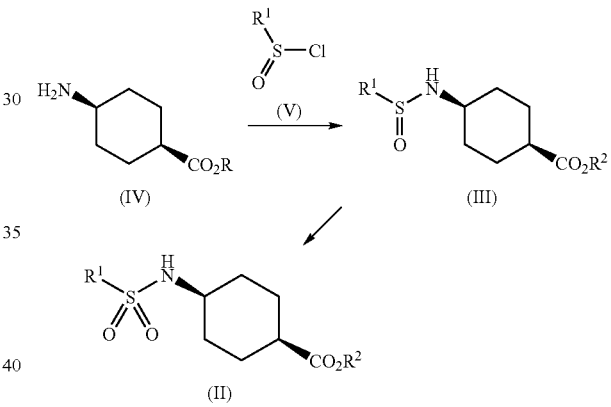

wherein $R^1$ and $R^2$ are the same as defined above.

(Step 1)

Compound (III) is obtained by reacting Compound (IV) with Compound (V), if desired, in the presence of a base.

Examples of the base are alkylamine such as triethylamine, N-methylmorpholine, dimethylaniline and the like and pyridine, and triethylamine is preferable.

Examples of a solvent is ethyl acetate, tetrahydrofuran, dimethylformamide and toluene, and ethyl acetate is preferable.

Reaction temperature is not limited but generally about 0 to 50° C. and preferably about 5 to 10° C.

Reaction time is not limited but generally about 1 to 50 hours and preferably about 13 hours.

(Step 2)

Compound (II) is obtained by oxidizing Compound (III).

Examples of an oxidant are a hydrogen peroxide solution, peracetic acid (with ammonium molybdate tetrahydrate $((NH_4)_6Mo_7O_{24}4H_2O)$ or sodium tungstate as a catalyst) and m-chloroperbenzoic acid, and a hydrogen peroxide solution (with ammonium molybdate tetrahydrate as a catalyst) is preferable.

Examples of a solvent are dimethylformamide, tetrahydrofuran, dimethylformamide and ethyl acetate, and dimethylformamide is preferable.

Reaction temperature is not limited but generally about 0 to 100° C. and preferably about 30 to 70° C.

Reaction time is not limited but generally 1 to 50 hours and preferably about 2 to 8 hours.

Compound (IV) may be a mixture of a cis isomer and a trans isomer. If the obtained compound in this step is a mixture of a cis isomer (Compound (II)) and a trans isomer, the mixture can be subjected to a conversion reaction to Compound (I) itself as mentioned above.

(Process 2) Conversion of Compound (IV) to Compound (IX)

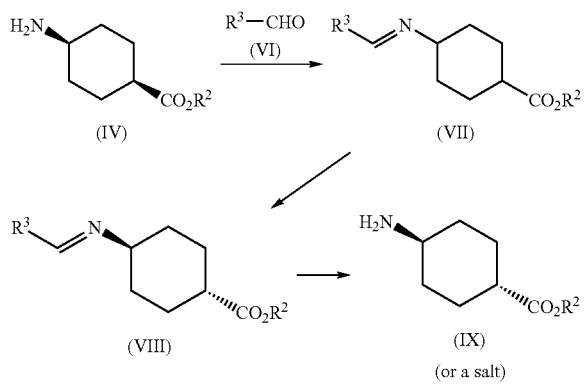

wherein $R^2$ is lower alkyl and $R^3$ is optionally substituted phenyl.

(Step 1)

Compound (VII) is obtained by reacting Compound (IV) with Compound (VI), if desired, in the presence of a base.

Examples of the base are an alkylamine such as triethylamine, pyridine, N-methylmorpholine and dimethylaniline, and triethylamine is preferable.

Examples of a solvent are acetonitrile, ethyl acetate, tetrahydrofuran and dioxane, and acetonitrile is preferable.

Reaction temperature is not limited but generally about 0 to 100° C. and preferably about 10 to 30° C.

Reaction time is not limited but generally 1 to 50 hours and preferably about 2 to 5 hours.

$R^3$ of Compound (VI) is optionally substituted phenyl. Substituents are exemplified by 1 to 3 substituents, preferably one substituent independently selected from the group of nitro, halogen such as F, Cl, Br and I, alkoxy, alkyl and amide. Nitro is preferable. These substituents may be substituted at any position on the phenyl ring and preferably at p-position.

(Step 2)

Compound (VIII) is obtained by reacting Compound (VII) with a base in an organic solvent. A cis isomer of a cyclohexane ring of Compound (VII) is isomerized to a trans isomer by this reaction.

A base is not limited as long as it can proceed with an isomerization of the cis isomer to the trans isomer and preferably exemplified by an alkaline metal lower alkoxide such as sodium methoxide, sodium ethoxide, potassium methoxide, potassium ethoxide and potassium tert-butoxide, an alkaline metal halide such as NaH, an alkaline metal amide such as lithium diisopropylamide (LDA) and $NaNH_2$. An alkaline metal lower alkoxide is preferable and sodium methoxide is more preferable.

The amount of a base is preferably about 1 to 10 mole equivalents and preferably about 2 to 3 mole equivalents relative to Compound (VII).

An organic solvent is not limited as long as it efficiently proceed to isomerize the cis isomer to the trans isomer. A preferable solvent is one in which a trans isomer, i.e. Compound (VIII) can be more efficiently crystallized than a cis isomer, i.e. Compound (VII). Examples of such solvent are above-mentioned aprotic solvent or alcohol such as methanol and ethanol, and methanol is more preferable.

Reaction temperature is not limited but generally about 25 to 100° C., and preferably about 40 to 70° C.

Reaction time is not limited but generally 1 to 50 hours and preferably about 3 to 5 hours.

Compound (VII) may be a mixture of a cis isomer and a trans isomer at an arbitrary ratio. This reaction gives Compound (VIII) in high yield because the cis isomer of Compound (VII) is efficiently isomerized to the trans isomer and the trans isomer is selectively precipitated. Isomerization rate is 90% or more, preferably 95% or more, and more preferably 98 to 100%. Compound (VII) wherein $R^3$ is p-nitrophenyl can be efficiently isomerized to the trans isomer by this step to give Compound (VIII).

Compound (VIII) is preferably recrystallized and examples of a solvent for recrystallization are the same as mentioned above. Even if the aforementioned isomerization rate is less than 100%, trans Compound (VIII) can be obtained in 100% by this recrystallization step.

(Step 3)

Compound (IX) is obtained by hydrolysis of Compound (VIII).

Examples of a solvent are ethyl acetate, acetonitrile, dimethylformamide, methanol and ethanol, and ethyl acetate is preferable.

Reaction temperature is not limited but generally about 0 to 50° C. and preferably about 10 to 30° C.

Reaction time is not limited but generally 1 to 50 hours and preferably about 2 to 5 hours.

Examples of a catalyst for this reaction are HCl, $H_2SO_4$, acetic acid, $CF_3COOH$, toluenesulfonic acid and p-toluenesulfonic acid, and preferably p-toluenesulfonic acid.

According to this step, Compound (IX), i.e., a trans isomer of Compound (IV), can be easily obtained by imidating Compound (IV), followed by isomerizing. Compound (IX) is useful as an intermediate of a medicament because it is easily utilized as an intermediate to produce NPYY5 receptor antagonists having various substituents which are on cyclohexane ring with trans configuration (referring to the above Patent Literature 1) by chemical modifications such as amidation of an ester group and/or sulfonylation of an amino group. Therefore, the above Compound (VII) and Compound (VIII) are also useful as intermediates.

(Process 3) Conversion of Compound (IX) to Compound (I)

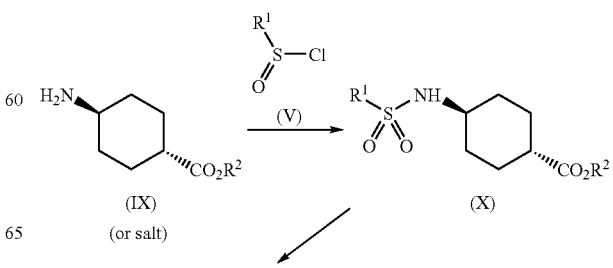

-continued

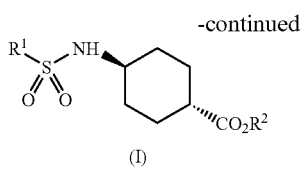

wherein each symbol is the same as defined above.

(Step 1)

Compound (X) is obtained by reacting Compound (IX) with Compound (V), if desired, in the presence of a base. This step may be performed according to the above-mentioned step for synthesis of Compound (III) from Compound (IV).

Any base can be used and examples are alkylamine such as triethyl amine, pyridine, N-methyl morpholine and dimethylaniline. Triethylamine is preferable. The amount of a base is preferably about 2.0 to 3.0 mole equivalent relative to Compound (IX).

The amount of Compound (V) is preferably about 1.0 to 1.5 mole equivalent relative to Compound (IX).

Any solvent can be used provided that it can dissolve or suspend a reaction substrate to give a reactive solution or slurry. Examples of a solvent are ethyl acetate, tetrahydrofuran, dimethylformamide and toluene and preferably ethyl acetate or dimethylformamide. The arbitrary amount of a solvent can be used as long as the reaction can be performed in the solution or slurry. For example, a solvent is preferably 1 to 10 times of volume relative to the total volume of a substrate and more preferably 3 times of volume (cc) relative to total weight (g) of a substrate.

Reaction temperature is not limited but generally about −10 to 50° C., preferably about 5 to 10° C.

Reaction time is not limited but generally about 1 hour to 5 days, preferably 1 hour to 2 days and more preferably about 1 to 3 hours.

Thus obtained product may be isolated or purified, or may be used for the next step without isolation or purification. The use of the product without isolation or purification is advantageous because the next step can be continuously performed.

(Step 2)

Compound (I) is obtained by oxidizing Compound (X). This step is performed according to the above step for synthesis of Compound (II) from Compound (III).

Examples of an oxidant are a hydrogen peroxide solution, peracetic acid (with ammonium molybdate tetrahydrate $((NH_4)_6Mo_7O_{24}4H_2O)$ or sodium tungstate or hydrate as a catalyst) and m-chloroperbenzoic acid and a hydrogen peroxide solution (with ammonium molybdate tetrahydrate $((NH_4)_6Mo_7O_{24}4H_2O)$ as a catalyst) is preferable.

The amount of a catalyst is preferably about 0.01 to 0.05 mole equivalent relative to Compound (X"). The amount of a peroxide is preferably about 1.0 to 2.0 mole equivalents relative to Compound (X").

Any solvent can be used provided that it can dissolve or suspend a reaction substrate to give a reactive solution or slurry. Examples of a solvent are dimethylformamide, tetrahydrofuran and ethyl acetate, and preferably dimethylformamide.

The arbitrary amount of a solvent can be used as long as the reaction can be carried out in the solution or slurry. For example, a solvent is preferably 1 to 10 times of volume relative to the total volume of a substrate and more preferably 3 times of volume (cc) relative to total weight (g) of a substrate.

Reaction temperature is not limited but generally about 0 to 100° C. and preferably about 20 to 80° C.

Reaction time is not limited but generally about 1 hour to 5 days, preferably 1 hour to 2 days and more preferably about 2 to 8 hours.

Thus-obtained Compound (I) can be converted to Compound (I') by hydrolysis according to the above.

(Process 4)

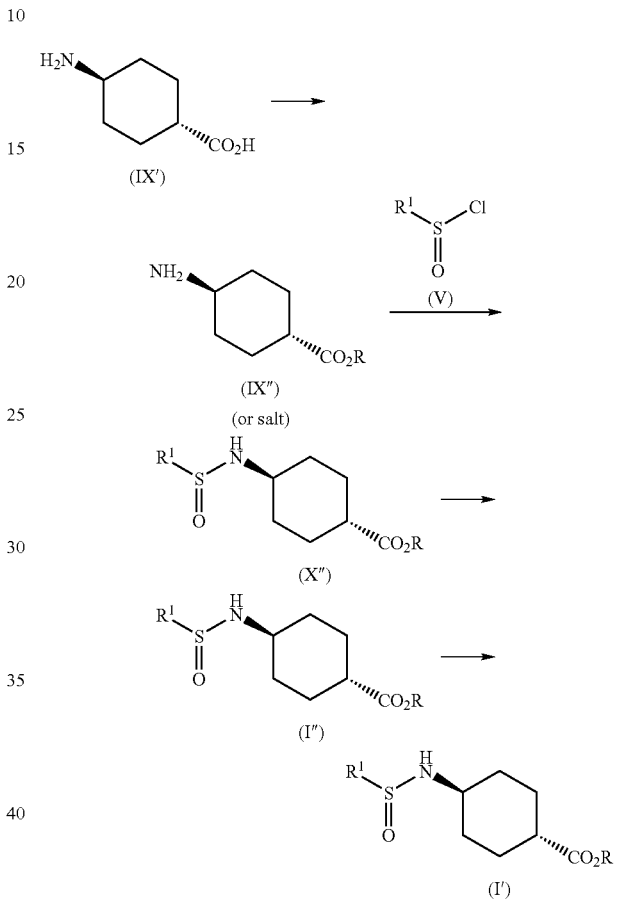

wherein R is hydrogen or a carboxyl-protective group and other each symbol is the same as defined above.

(Step 1)

In this step, if desired, Compound (IX') is protected by a protective group R to give Compound (IX"), i.e., a protected trans cyclohexane carboxylic acid compound. If the next reaction is not influenced by the substituents, a protective group R need not to be introduced and a free carboxylic acid compound may be subjected to Step 2.

A carboxyl-protective group is not limited as long as it is usually used and Examples are methyl, ethyl, t-butyl, phenyl, benzyl and triphenylmethyl. If methyl is used as a protective group, Compound (IX") can be obtained by reacting Compound (IX') with a thionyl chloride in methanol.

The amount of Compound (V) is about 0.6 to 2.0 mole equivalent relative to Compound (IX').

Any solvent can be used provided that it can dissolve or suspend a reaction substrate to give a reactive solution or slurry.

The arbitrary amount of a solvent can be used as long as the reaction can be performed in the solution or slurry. For example, a solvent is preferably 1 to 10 times of volume relative to the total volume of a substrate and more preferably 3 times of volume (cc) relative to total weight (g) of a substrate.

Reaction temperature is preferably 0 to 60° C.

As a method for isolation of the product after the reaction, carrying out the crystallization is preferable and acetonitrile or toluene is preferably used as a solvent.

Reaction time is preferably about 1 hour to 5 days and more preferably about 2 hours to 2 days.

Thus obtained product may be isolated or purified, and the product without isolation or purification may be subjected to the next step. The use of the product without isolation or purification is advantageous because the next step can be continuously performed.

(Step 2)

In this step, Compound (X") is obtained by reacting Compound (IX") with Compound (V) and a base.

Reaction conditions are the same as those in the above Process 3, Step 1.

(Step 3)

In this step, Compound (I") is obtained by oxidizing Compound (X").

Reaction conditions are the same as those in the above Process 3, Step 2.

Thus-obtained product may be isolated or purified. The product without isolation or purification may be subjected to the next step. The use without isolation or purification is advantageous because the next step can be continuously performed.

Compound (I") wherein R is hydrogen need not to be subjected to the next step and can be converted to Compound (XII) according to Process 5 mentioned below.

(Step 4)

In this step, Compound (I') is obtained by deprotective Compound (I") wherein R is a carboxyl-protective group.

It is preferred to use an appropriate reagent to deprotect the protective group introduced in Step 1.

For example, when methyl is used as a protective group, Compound (I") may be reacted with a base such as sodium methoxide and water. The amount of a base is preferably about 2.0 to 3.0 mole equivalent relative to Compound (I").

Any solvent can be used provided that it can dissolve or suspend a reaction substrate to give a reactive solution or slurry.

The arbitrary amount of a solvent can be used as long as the reaction can be performed in the solution or slurry. For example, a solvent is preferably 1 to 10 times of volume relative to the total volume of a substrate.

Reaction temperature is preferably 0 to 40° C.

Reaction time is preferably about 1 hour to 5 days and preferably about 2 hours to 24 hours.

Thus-obtained product may be isolated or purified. The product without isolation or purification may be subjected to the next step. The use without isolation or purification is advantageous because the next step can be continuously performed.

(Process 5) Conversion of Compound (I') to Compound (XII)

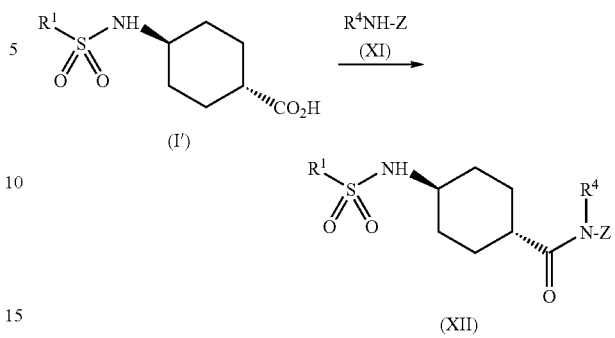

wherein $R^1$ is lower alkyl; $R^4$ is hydrogen or lower alkyl; Z is optionally substituted lower alkyl, optionally substituted lower alkenyl, optionally substituted amino, optionally substituted lower alkoxy, optionally substituted carbocyclyl, or optionally substituted heterocyclyl.

Examples of lower alkyl of $R^4$ are the same as those represented by $R^1$. $R^4$ is preferably hydrogen.

Examples of the substituent in "optionally substituted lower alkyl" of Z are (1) halogen; (2) cyano; (3) the following groups (i) to (xvi): (i) hydroxy, (ii) lower alkoxy, (iii) mercapto, (iv) lower alkylthio, (v) acyl, (vi) acyloxy, (vii) carboxy, (viii) lower alkoxycarbonyl, (ix) imino, (x) carbamoyl, (xi) thiocarbamoyl, (xii) lower alkyl carbamoyl, (xiii) lower alkylthio carbamoyl, (xiv) amino, (xv) lower alkylamino or (xvi) heterocyclylcarbonyl, which may be optionally substituted by at least one of groups selected from the Substituent Group β defined below.

Substituent Group α is a group of (1) halogen; (2) oxo; (3) cyano; (4) nitro; (5) imino optionally substituted by lower alkyl or hydroxy; (6) the following groups (i) to (xxi): (i) hydroxy, (ii) lower alkyl, (iii) lower alkenyl, (iv) lower alkoxy, (v) carboxyl, (vi) lower alkoxycarbonyl, (vii) acyl, (viii) acyloxy, (ix) imino, (x) mercapto, (xi) lower alkylthio, (xii) carbamoyl, (xiii) lower alkyl carbamoyl, (xiv) cycloalkylcarbamoyl, (xv) thiocarbamoyl, (xvi) lower alkylthiocarbamoyl, (xvii) lower alkylsulfinyl, (xviii) lower alkylsulfonyl, (xix) sulfamoyl, (xx) lower alkylsulfamoyl and (xxi) cycloalkylsulfamoyl, which may be optionally substituted by at least one of groups selected from Substituent Group β; (7) the following groups (i) to (v): (i) cycloalkyl, (ii) cycloalkenyl, (iii) cycloallyloxy, (iv) amino and (v) alkylenedioxy, which may be optionally substituted by a substituent selected from the group of Substituent β, lower alkyl, lower alkoxy-lower alkyl, optionally protected hydroxy-lower alkyl; and (8) the following groups: (i) phenyl, (ii) naphtyl, (iii) phenoxy, (iv) phenyl-lower alkoxy, (v) phenylthio, (vi) phenyl-lower alkylthio, (vii) phenylazo, (viii) heterocyclyl, (ix) heterocyclyloxy, (x) heterocyclylthio, (xi) heterocyclylcarbonyl and (xii) heterocyclylsulfonyl, which may be optionally substituted by a substituent selected from the group of Substituent β, lower alkyl, halogeno-lower alkyl and/or oxo.

Substituent Group β is a group of halogen, optionally protected hydroxy, mercapto, lower alkoxy, lower alkenyl, amino, lower alkylamino, lower alkoxycarbonyl amino, lower alkylthio, acyl, carboxyl, lower alkoxycarbonyl, carbamoyl, cyano, cycloalkyl, phenyl, phenoxy, lower alkyl phenyl, lower alkoxy phenyl, halogenophenyl, naphtyl and heterocyclyl.

"Lower alkenyl" includes C2 to C10, preferably C2 to C8 and more preferably C3 to C6 straight or branched alkenyl which has at least one double bond at arbitrary position. Examples are vinyl, propenyl, isopropenyl, butenyl, isobutenyl, prenyl, butadienyl, pentenyl, isopentenyl, pentadienyl, hexenyl, isohexenyl, hexadienyl, heptenyl, octenyl, nonenyl, and decenyl. Substituents in "optionally substituted lower alkenyl" are exemplified by halogen, lower alkoxy, lower alkenyl, amino, lower alkylamino, lower alkoxycarbonyl amino, lower alkylthio, acyl, carboxy, lower alkoxycarbonyl, carbamoyl, cyano, cycloalkyl, phenyl, lower alkyl phenyl, lower alkoxy phenyl, naphtyl and/or heterocyclyl.

Substituents in "optionally substituted amino" are exemplified by the above-mentioned substituent selected from Substituent Group β, optionally substituted benzoyl and/or optionally substituted heterocyclylcarbonyl wherein the substituents are hydroxy, lower alkyl, lower alkoxy and/or lower alkylthio.

"Lower alkoxy" means oxy group combined with the above "lower alkyl" and examples are methoxy, ethoxy and i-propoxy.

Substituents in "optionally substituted lower alkoxy" are exemplified by at least one of groups selected from the above Substituent Group β and preferable examples are phenyl, lower alkyl phenyl, lower alkoxy phenyl, naphtyl or heterocyclyl.

"Carbocyclyl" includes "cycloalkyl", "cycloalkenyl", "bicycloalkyl" and "aryl".

"Cycloalkyl" includes C3 to C8 and preferably C5 or C6 cyclic alkyl. Examples are cyclopropyl, cyclobutyl, cyclopentyl, cyclohexyl, cycloheptyl and cyclooctyl.

"Cycloalkenyl" includes groups which have at least one double bond at arbitrary position in the above cycloalkyl and examples are cyclopropenyl, cyclobutenyl, cyclopentenyl, cyclohexenyl and cyclohexadienyl.

"Bicycloalkyl" includes C5 to C8 alicyclic groups wherein the two rings share two or more atoms and which are given by removing one hydrogen from C5 to C8 alicyclic group. Examples are bicyclo[2.1.0]pentyl, bicyclo[2.2.1]heptyl, bicyclo[2.2.2]octyl and bicyclo[3.2.1]octyl.

"Aryl" means monocyclic or polycyclic aromatic carbocyclic group and includes phenyl, naphtyl, anthryl, and phenanthryl. "Aryl" includes aryl which is fused with another non-aromatic carbocycle and it is exemplified by indanyl, indenyl, biphenylyl, acenaphtyl, tetrahydronaphtyl and fluorenyl. Phenyl is preferable.

Examples of substituents in "optionally substituted carbocyclyl" are at least one of groups selected from the group of the above Substituent Group α and Substituent Group β. "Carbocyclyl" may be substituted with them at any arbitrary positions.

"Heterocyclyl" includes heterocyclic groups which contain at least one hetero atoms arbitrarily selected from the group of O, S and N, and examples are 5 to 6 membered heteroaryl such as pyrrolyl, imidazolyl, pyrazolyl, pyridyl, pyridazinyl, pyrimidinyl, pyrazinyl, triazolyl, triazinyl, tetrazolyl, isoxazolyl, oxazolyl, oxadiazolyl, isothiazolyl, thiazolyl, thiadiazolyl, furyl and thienyl; fused bicyclic heterocyclyl such as indolyl, isoindolyl, indazolyl, indolizinyl, indolinyl, isoindolinyl, quinolyl, isoquinolyl, cinnolinyl, phthalazinyl, quinazolinyl, naphthyridinyl, quinoxalinyl, purinyl, pteridinyl, benzopyranyl, benzimidazolyl, benzisoxazolyl, benzoxazolyl, benzoxadiazolyl, benzisothiazolyl, benzothiazolyl, benzothiadiazolyl, benzofuryl, isobenzofuryl, benzothienyl, benzotriazolyl, imidazopyridyl, triazolopyridyl, imidazothiazolyl, pyrazinopyridazinyl, quinazolinyl, dihydropyridyl, tetrahydroquinolyl and tetrahydrobenzothienyl; fused tricyclic heterocyelyl such as carbazolyl, acridinyl, xanthenyl, phenothiazinyl, phenoxatiinyl, phenoxazinyl and dibenzofuryl; non-aromatic heterocyclyl such as dioxanyl, thiiranyl, oxiranyl, oxathiolanyl, azetidinyl, thianyl, pyrrolidinyl, pyrrolinyl, imidazolidinyl, imidazolinyl, pyrazolidinyl, pyrazolinyl, piperidyl, piperazinyl, morpholinyl, morpholino, thiomorpholinyl, thiomorpholino, dihydropyridyl, tetrahydrofuryl, tetrahydropyranyl, tetrahydrothiazolyl and tetrahydroisothiazolyl.

Heterocyclyl which is fused with a ring other than heterocyclic ring such as benzothiazolyl may have a bonding radical on any ring.

Examples of the substituent in "optionally substituted heterocyclyl" are the same as those in the above "optionally substituted carbocyclyl".

Compound (XII), a prodrug or a pharmaceutically acceptable salt or solvate thereof can be obtained by reacting Compound (I') with Compound (XI). This reaction can be performed according to amidation reaction described in the above Patent Literature 1 or the like.

Generally, Compound (I') is reacted with an activated Compound (XI) such as a corresponding acid halide (eg. reaction with thionyl chloride, oxalyl chloride or phosphorus oxychloride), a corresponding acid anhydride, a corresponding activated ester or the like at about 0° C. to 100° C. for about 3 minutes to 10 hours. Tetrahydrofuran, dimethylformamide, diethyl ether, dichloromethane, toluene, benzene, xylene, cyclohexane, hexane, chloroform, ethyl acetate, butyl acetate, pentane, heptane, dioxane, acetone, acetonitrile, water or the mixture thereof can be used as a solvent, and toluene or tetrahydrofuran is preferable. If necessary, a base (triethylamine or pyridine etc.), thionyl chloride, an acid halide (such as thionyl chloride, oxalyl chloride or phosphorus oxychloride), an acid anhydride or an activated ester can be used as an activating agent.

As alternative process, Compound (I') is reacted with Compound (XI) in a suitable solvent (such as tetrahydrofuran, dimethylformamide, diethyl ether, dichloromethane, toluene, benzene, xylene, cyclohexane, hexane, chloroform, ethyl acetate, butyl acetate, pentane, heptane, dioxane, acetone, acetonitrile, water or the mixture thereof) in the presence of a condensing agent at about 0° C. to 100° C. for about 3 minutes to 10 hours to obtain a target compound. As a condensing agent, 1,1-carbonyldiimidazole, dicyclohexylcarbodiimide or water-soluble carbodiimide (1-ethyl-3-(3'-dimethylaminopropyl)carbodiimide) and the like can be used.

Compound (XII) is useful as, for example, a NPY Y5 receptor antagonist.

Examples of a pharmaceutically acceptable salt for Compound (XII) are salts of a mineral acid such as hydrochloric acid, sulfuric acid, nitric acid, phosphoric acid; salts of an organic acid such as paratoluenesulfonic acid, methansulfonic acid, oxalic acid and citric acid; salts of an organic base such as ammonium, trimethylammonium and triethylammonium; salts of an alkaline metal such as sodium, potassium and the like and salts of an alkaline earth metal such as calcium, magnesium and the like. Examples of solvate of Compound (XII) are hydrate, alcoholate and the like. A prodrug of Compound (XII) means derivatives which can be converted to Compound (XII) by chemical decomposition or metabolism. Methods for selecting or producing appropriate prodrugs are described in Design of Prodrugs, Elsevier, Amsterdam 1985, for example.

The present invention provides each step of the above-mentioned processes, all of the processes comprising combination of the steps arbitrarily selected, and intermediates of such processes.

EXAMPLES
The present invention is further explained by the following Examples. Abbreviations in Examples mean as follows:
Me: methyl
Et: ethyl
Ac: acetyl
DMF: dimethylformamide
THF: tetrahydrofuran
p-TsOH: para-toluenesulfonic acid
WSCD: water-soluble carbodiimide
BtOH: N-hydroxybenzotriazole
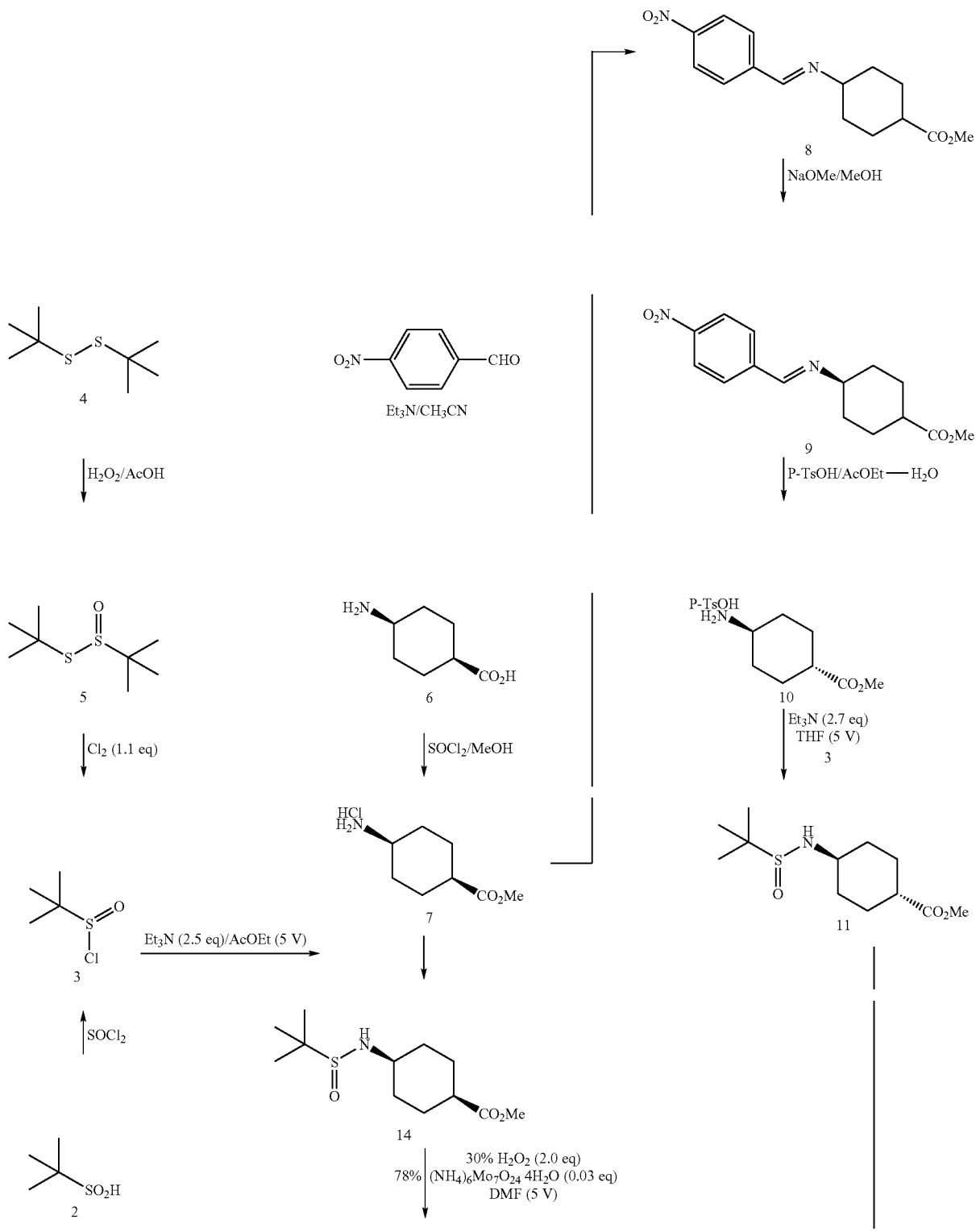

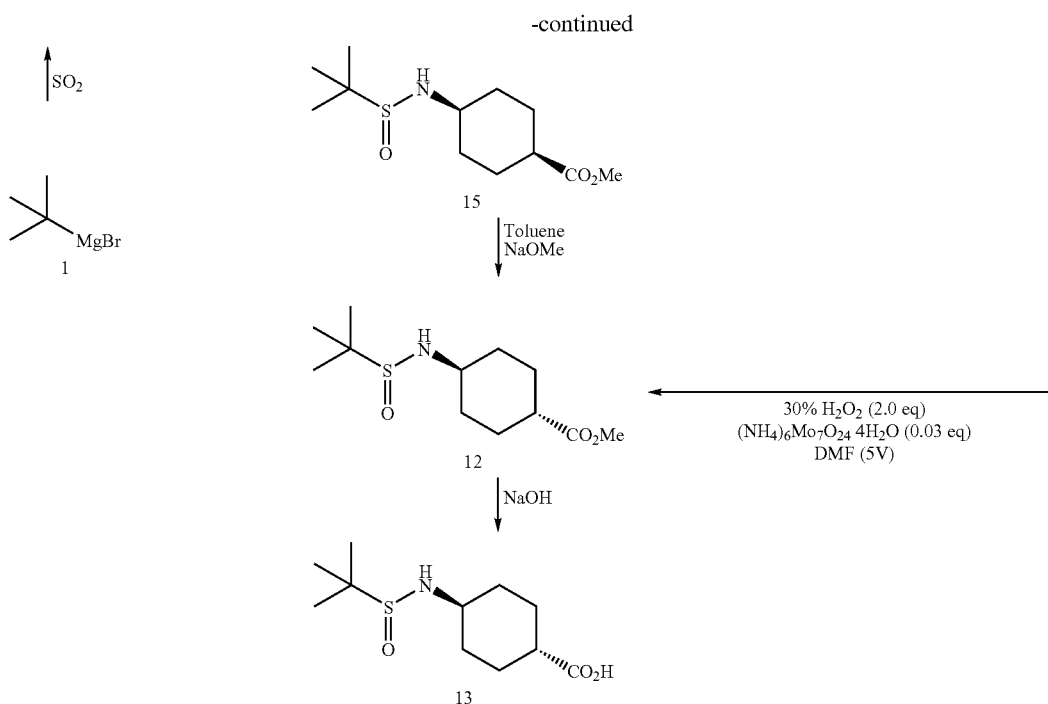

Reference Example 1

Synthesis of 2-methylpropane-2-sulfinylchloride (3)

(1) 2-Methylpropane-2-sulfinic acid (2)

Sulfurous acid gas (162 g, 1.23 eq) was introduced into a solution of t-butyl magnesium chloride (1) in tetrahydrofuran (2 mol/L, 1 kg, 2.06 mol) with cooling at 2 to 20° C. Two lots obtained in the same manner were combined, poured into a mixture of ice, concentrated hydrochloric acid and toluene, and extracted. Toluene layer was washed with saturated brine and each of aqueous layer was extracted with toluene. Toluene layers were dried over sodium sulfate, concentrated under reduced pressure to obtain a solid residue of (2) (396 g, 78.7%).

(2) 2-Methylpropane-2-sulfinyl chloride (3)

Thionyl chloride (460 mL) was added dropwise to a solution of (2) (700 g, 5.729 mol) in anhydrous tetrahydrofuran (3 L) at ice cooling and the mixture was stirred for 30 minutes at the same temperature. The reaction mixture was concentrated under reduced pressure to obtain a solid residue (3) (900 g).

$^1$H NMR (CDCl$_3$): δ 1.41 (s, 3 H).

(3) Tert-butyl Tert-butane Thiosulfinate (5)

30% hydrogen peroxide solution (128 mL) was added dropwise to a solution of tert-butyl disulfide (4) (178.36 g, 1 mol) in acetic acid (357 mL) over 38 minutes at 30 to 37° C. After the mixture was stirred for 3 hours at same temperature, 7.5% aqueous solution of sodium sulfite (900 mL) was added over 19 minutes at 6 to 13° C. Ethyl acetate (1.3 L) was added to the reaction mixture and the mixture was extracted twice. Separated organic layer was neutralized with aqueous solution of an alkaline and washed with water. The solvent was concentrated under reduced pressure to obtain (5) (190.4 g, 98%).

$^1$H NMR (CDCl$_3$): δ 1.38 (s, 3 H), 1.56 (s, 3 H)

(4) 2-Methylpropane-2-Sulfinyl chloride (3)

a) Chlorine gas (65 g, 1.1 eq) was introduced into tert-butyl tert-butane thiosulfinate (5) (190.4 g, 0.84 mol) at 11 to 20° C. The mixture was stirred for 30 to 120 minutes at room temperature and distilled under reduced pressure to obtain (3) (bp. 13 mmHg 7-13, 34-35° C., 105.7 g, 90%)

$^1$H NMR (CDCl$_3$): δ 1.41 (s, 3 H)

b) Chlorine gas (77 g, 1.1 eq) was introduced into a solution of tert-butyl tert-butane thiosulfinate (5) (162.5 g, 0.98 mol) in dichloromethane (665 mL) at 11 to 20° C. Dichloromethane was concentrated under reduced pressure and the obtained residue was distilled under reduced pressure to obtain (3) (bp. 18 mmHg 7-13, 50-56° C., 130.0 g, 94.3%).

Reference Example 2

Synthesis of methyl cis-4-amino-1-cyclohexane carboxylate hydrochloride (7)

Thionyl chloride (301 mL, 0.6 eq) was added dropwise to a suspension of cis-4-amino-1-cyclohexane carboxylic acid (6) (984 g, 6.87 mol) in methanol (4.82 L) and stirred for 6 hours at room temperature, and the mixture was allowed to be stand for 3 days. The reaction mixture was concentrated under reduced pressure and isopropyl ether was added to the mixture. The appeared crystals were collected by filtration to obtain methyl cis-4-amino-1-cyclohexane carboxylate hydrochloride (1086 g, 81.6%). The mother liquor was concentrated under reduced pressure and methanol (50 mL) and isopropyl ether (1.0 mL) were added to the residue. The appeared crystals were collected by filtration to obtain second crystals of (7) (94 g, 7.0%).

mp. 172-174° C.

Anal. Calcd. for $C_8H_{16}NO_2Cl$: C, 49.61; H, 8.33; N, 7.23; Cl, 18.31. Found: C, 49.17; H, 8.27; N, 7.33; Cl, 18.19, $H_2O>0.1\%$.

1H NMR ($CD_3OD$): δ 1.40-1.50 (m, 4 H), 1.85-1.95 (m, 2H), 2.03-2.20 (m, 2H), 2.70-2.75 (m, 1H), 3.10-3.25 (m, 1H), 3.70 (s, 3H)

Example 1

Synthesis of methyl trans-4-(2-methylpropane-2-sulfonylamino)cyclohexane carboxylate (12) (via Compound (15))

(1) Methyl cis-4-(2-methylpropane-2-sulfinylamino)cyclohexane carboxylate (14)

Triethylamine (272 mL) was added dropwise to a suspension of methyl cis-4-amino-1-cyclohexane carboxylate hydrochloride (7) (151 g, 0.78 mol) and 2-methylpropane-2-sulfinyl chloride (3) (120.8 g, 1.1 eq) in ethyl acetate (755 mL) at 6 to 9° C. The mixture was stirred for an hour at the same temperature and poured into diluted hydrochloric acid. The mixture was extracted with ethyl acetate (750 mL×2) and each of organic layers was washed with water, 5% aqueous solution of sodium bicarbonate, water and brine, successively. The solvent was concentrated under reduced pressure to obtain oily (14) (222.7 g, 1.09%).

(2) Methyl cis-4-(2-methylpropane-2-sulfonylamino)cyclohexane carboxylate (15)

After an aqueous solution of ammonium molybdate tetrahydrate (28.9 g, 0.03 eq) (100 mL) was added to a solution of (14) (222.7 g) in DMF (1.0 L), 30% hydrogen peroxide solution (177 g, 2 eq) was added dropwise to the mixture over 30 minutes at 30 to 43° C. The mixture was stirred for 2 hours at the same temperature and poured into water (10 L). The mixture was stirred with cooling and the appeared crystals were collected by filtration. After the crystals were dissolved in ethyl acetate (1.8 L), the solution was dried over magnesium sulfate etc. and concentrated under reduced pressure. Isopropyl ether was added to the resultant and the appeared crystals were collected by filtration and dried to obtain (15) (171.2 g, 79% yield from (7)).

mp. 162-4° C.,

Anal. Calcd. for $C_{12}H_{23}NO_4S$: C, 51.96; H, 8.36; N, 5.05; S, 11.56. Found: C, 51.80; H, 8.37; N, 5.00; S, 11.49, $H_2O>0.1\%$.

$^1$H NMR ($CDCl_3$): δ 1.39 (s, 3H), 1.60-2.00 (m, 8H), 2.45-2.55 (m, 1H), 3.45-3.55 (m, 1H), 3.69 (s, 3H), 3.95 (d, J=12 Hz, 1H)

(3) Methyl trans-4-(2-methylpropane-2-sulfonylamino)cyclohexane carboxylate (12)

To a suspension of powder sodium methylate (7.06 g, 2.5 eq) in toluene (145 mL) was added methyl formate (1.61 mL, 0.5 eq). After the mixture was stirred for an hour at room temperature, (15) (14.5 g, 52.3 mmol) was added to the mixture. The mixture was heated under reflux for 2 hours 25 minutes, cooled and poured into 0.76 mol/L hydrochloric acid (344 mL). The mixture was extracted with ethyl acetate (300 mL×2), and the obtained organic layer was washed with water and brine, and dried over sodium sulfate. The solvent was removed under reduced pressure to obtain 14.42 g of crystalline residue (cis:trans=3:97). The residue was recrystallized from toluene to obtain (12) (10.2 g, 70% from (15)).

Comparison Example 1

Isomerization of (15) to (12) in Methanol

Methanol (75 mL) and methyl formate (4.44 mL, 0.5 eq) were added to 28% solution of sodium methylate in methanol (69.45 g, 2.5 eq). After the mixture was stirred for an hour at room temperature, methyl cis-4-(2-methylpropane-2-sulfonylamino)cyclohexane carboxylate (15) (40 g, 0.144 mol) was added to the mixture. The mixture was heated under reflux for 2 hours 20 minutes, cooled and poured into 1.2 mol/L hydrochloric acid (600 mL). The appeared crystals were collected by filtration (37.31 g, cis:trans=18:82).

24.81 g of the crystals were recrystallized from toluene to obtain 15 g of methyl trans-4-(2-methylpropane-2-sulfonylamino)cyclohexane carboxylate (12) (56% yield from (15)).

mp, 141-143° C.,

Anal. Calcd. for $C_{12}H_{23}NO_4S$: C, 51.96; H, 8.36; N, 5.05; S, 11.56. Found: C, 51.67; H, 8.27; N, 5.02; S, 11.46, $H_2O>0.1\%$.

1H NMR ($CDCl_3$): δ 1.20-1.40 (m, 2H), 1.39 (s, 3H), 1.42-1.62 (m, 2H), 2.0-2.32 (m, 5H), 3.20-3.35 (m, 1H), 3.67 (s, 3H), 3.99 (d, J=9 Hz, 1H)

Example 2

Synthesis of trans-4-(2-methylpropane-2-sulfonylamino)cyclohexane carboxylic acid (13)

An aqueous solution (4.4 L) of sodium hydroxide (441 g, 2.5 eq) was added dropwise to a solution of methyl trans-4-(2-methylpropane-2-sulfonylamino)cyclohexane carboxylate (12) (1222 g, 4,407 mol) in methanol (2.45 L) over 30 minutes at 4 to 12° C. The mixture was stirred for an hour at 12 to 36° C. and methanol was removed under reduced pressure. The pH value of the residue was adjusted to 9.7 with hydrochloric acid and the mixture was washed with ethyl acetate (4.5 L). The organic layer was extracted with water (1 L). Aqueous layers were combined, acidified with hydrochloric acid, and extracted with ethyl acetate (5 L, 4 L). Each of organic layer was washed with brine, dried over sodium sulfate and concentrated under reduced pressure. The appeared crystals were collected by filtration and washed with IPE to obtain (13) (1012 g, 87.2%).

mp. 201-203° C.

Anal. Calcd. for $C_{11}H_{21}NO_4S$: C, 50.17; H, 8.04; N, 5.32; S, 12.18. Found. C, 49.88; H, 8.02; N, 5.32; S, 12.23.

$^1$H NMR ($CDCl_3$): δ 1.16-1.32 (m, 2H), 1.39 (s, 3H), 1.49-1.62 (m, 2H), 2.0-2.32 (m, 5H), 3.27 (m, 1H), 3.67 (s, 3H), 3.99 (d, J=9 Hz, 1H)

Example 3

Synthesis of trans-4-(2-methylpropane-2-sulfonylamino)cyclohexane carboxylic acid (13) (One-pot process from (15))

To a suspension of powder sodium methylate (48.69 g, 2.5 eq) in toluene (1.0 L), was added methyl formate (11.11 mL, 0.5 eq) and the mixture was stirred for an hour at room temperature. To a mixture was added methyl 4-(2-methylpropane-2-sulfonylamino)cyclohexane carboxylate (15) (100 g, 0.361 mol). The mixture was heated under reflux for 2 hours 30 minutes (Notes: Compound (12) was precipitated at this time) and cooled to 40° C. Tetrabutylammonium bromide (5.81 g, 0.025 eq) and water (450 mL) were added to the mixture and the mixture was stirred for 1 hour 30 minutes at 35 to 40° C. Aqueous layer was separated and acidified with hydrochloric acid. The appeared crystals were collected by filtration, washed with water and dried to obtain (13) (87.8 g, 92.5% from (15)).

mp, 201-203° C.
$^1$H NMR (CDCl$_3$): δ 1.16-1.32 (m, 2H), 1.39 (s, 3H), 1.49-1.62 (m, 2H), 2.0-2.32 (m, 5H), 3.27 (m, 1H), 3.67 (s, 3H), 3.99 (d, J=9 Hz, 1H)

Example 4

Synthesis of methyl trans-4-amino-1-cyclohexane carboxylate p-toluenesulfonate (10)

(1) Methyl 4-(nitrobenzylidene aminocyclohexa)-carboxylate (8)

Triethylamine (848 mL, 1 eq) was added dropwise to a solution of methyl cis-4-amino-1-cyclohexane carboxylate hydrochloride (8) (1178 g, 6.08 mol) and p-nitrobenzaldehyde (919 g, 1 eq) in acetonitrile (5.89 L) and the mixture was stirred for 3 hours at the same temperature. The reaction mixture was concentrated under reduced pressure and the resultant was extracted with methyl acetate (7 L). The organic layer was washed with water (7 L, 3 L) and saturated brine, successively, and dried over sodium sulfate and magnesium sulfate. The mixture was concentrated under reduced pressure and toluene (1 L) was added to the residue. The mixture was concentrated under reduced pressure to obtain crystalline residue (8) (2.2 kg).

(2) Methyl(S)-4-(nitrobenzylidene aminocyclohexa)-carboxylate (9)

Methanol (4 L) and methyl formate (188 mL, 0.5 eq) were added to 28% solution of sodium methylate in methanol (3.01 L, 2.5 eq) and the mixture was stirred for 40 minutes at room temperature. A solution of (8) (2.2 kg, 6.06 mol) in methanol (1.6 L) was added to the mixture and the mixture was heated under reflux at 50° C. for 4 hours. The reaction mixture was allowed to ice-cooling and the appeared crystals were collected by filtration and washed with cooled methanol (1.6 L×2) to obtain (9) (1461 g, 82.7%).

mp. 176-177,
Anal. Calcd. for C$_{15}$H$_{18}$N$_2$O$_4$: C, 60.05; H, 6.25; N, 9.65. Found: C, 61.79; H, 6.14; N, 9.76.
$^1$H NMR (CDCl$_3$): δ 1.5-1.7 (m, 4H), 1.8-2.1 (m, 4H), 2.3-2.4 (m, 1H), 3.2-3.3 (m, 1H), 3.7 (s, 3H), 7.89, 8.26 (q, J=9 Hz, 4H), 8.4 (s, 1H)

(3) Methyl trans-4-amino-1-cyclohexane carboxylate p-toluene sulfonate (10)

Crystals of (9) (1460 g) were added to a mixture of p-toluenesulfonic acid monohydrate (1052 g, 1.1 eq), ethyl acetate (8 L) and water (511 mL) at room temperature and the mixture was washed with ethyl acetate (2.2 L). The mixture was stirred for 1.5 hours at room temperature and poured into cooled ethyl acetate (32 L). The appeared crystals were collected by filtration and washed with ethyl acetate (2 L×2) to obtain (10) (1559 g, 94.1%).

mp. 183-185° C.,
Anal. Calcd. for C$_{15}$H$_{23}$NO$_5$S: C, 54.69; H, 7.04; N, 4.25; S, 9.73. Found: C, 54.36; H, 6.98; N, 4.51; S, 9.65.
$^1$H NMR (CDCl$_3$): δ 1.3-1.6 (m, 4H), 2.0-2.15 (m, 4H), 2.3 (m, 1H), 2.37 (s, 3H), 3.05 (m, 1H), 3.3 (m, 1H), 3.66 (s, 3H), 7.70, 7.24 (q, J=8.1 Hz, 4H)

Example 5

Synthesis of methyl trans-4-(2-methylpropane-2-sulfonylamino)cyclohexane carboxylate (12) (via Compound (II))

(1) Methyl trans-4-(2-methylpropane-2-sulfinylamino)cyclohexane carboxylate (11)

Triethylamine (1658 mL, 2.7 eq) was added dropwise to a solution of 2-methylpropane-2-sulfinyl chloride (3) (900 g, 1.3 eq) and methyl trans-4-amino-1-cyclohexane carboxylate p-toluenesulfonate (10) (1452 g, 4.407 mol) in tetrahydrofuran (9.5 L) with ice-cooling. The mixture was stirred for 1.5 hours at room temperature, poured into water (9.5 L) and extracted with ethyl acetate (9.5 L, 5 L). Each of organic layer was washed with brine twice, dried over sodium sulfate, and concentrated under reduced pressure to obtain (11) (1.26 kg).

(2) Methyl trans-4-(2-methylpropane-2-sulfonylamino)cyclohexanecarboxylate (12)

An aqueous solution (576 mL) of ammonium molybdate tetrahydrate (163 g, 0.03 eq) was added to a solution of (11) (1.26 kg) in DMF (5.76 L). To the mixture was added dropwise 30% hydrogen peroxide solution (749 g, 1.5 eq) over 39 minutes at 25 to 44° C. The mixture was stirred for 47 minutes at the same temperature and 30% hydrogen peroxide solution (250 g, 0.5 eq) was added dropwise over 3 minutes at 38 to 39° C. The mixture was stirred for 30 minutes at the same temperature, poured into iced water (23 L), and stirred with cooling. The appeared crystals were collected by filtration to obtain (12) (1222 g, 100% from (10)).

$^1$H NMR (CDCl$_3$): δ 1.20-1.7 (m, 4 H), 1.39 (s, 3H), 2.00-2.15 (m, 2H), 2.15-2.23 (m, 3H), 3.10-3.35 (m, 1H), 3.67 (s, 3H), 3.80 (d, J=12 Hz, 1H)

Example 6

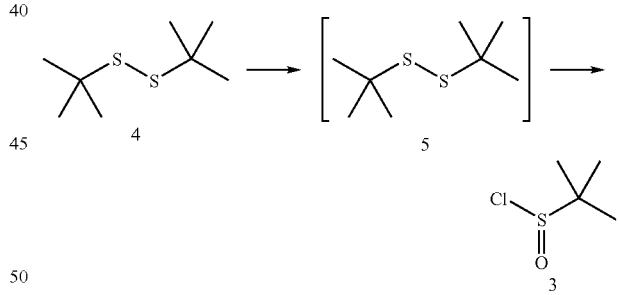

To the mixture of 27.0 kg of Compound (4) and 56.6 kg of glacial acetic acid was added dropwise 6.2 kg of 35% hydrogen peroxide solution with stirring over 65 minutes at 25° C. to 35° C. and the mixture was stirred for 87 minutes at 32° C. to 35° C. To the mixture was added dropwise 6.2 kg of 35% hydrogen peroxide solution with stirring over 60 minutes at 32° C. to 34° C. and stirred for 82 minutes at 34° C. to 35° C. To the mixture was added dropwise 6.2 kg of 35% hydrogen peroxide solution with stirring over 60 minutes at 35° C. to 36° C. and the mixture was stirred for 135 minutes at 36° C. to 37° C. To the reaction mixture was added 81.0 kg of water and 62.2 kg of 20% aqueous solution of sodium hydrogensulfite was added dropwise to the mixture at 17° C. to 28° C. to remove remained peroxide. After the mixture was cooled to 9° C., 79.6 kg of 48% aqueous solution of sodium hydroxide was added dropwise to the mixture over 136 minutes at 9° C. to 15° C. To the mixture was added 73.1 kg of ethyl acetate and separated. The organic layer was washed with 85.1 kg of 5% sodium hydrogencarbonate and 81.0 kg of water, successively. The first aqueous layer was washed with 24.4 kg of ethyl acetate and the combined organic layer was concentrated to the extent of 1.0% or less of ethyl acetate and 0.3% or less of water.

After the mixture was divided into 8 portions, 1.3 kg of chlorine gas was introduced into one portion over 145 minutes at 9° C. to 17° C. The mixture was stirred for 100 minutes at 8° C. to 13° C. and distilled under reduced pressure to obtain 2.45 kg of Compound (3) (92.1% from dibutyldisulfide)

Example 7

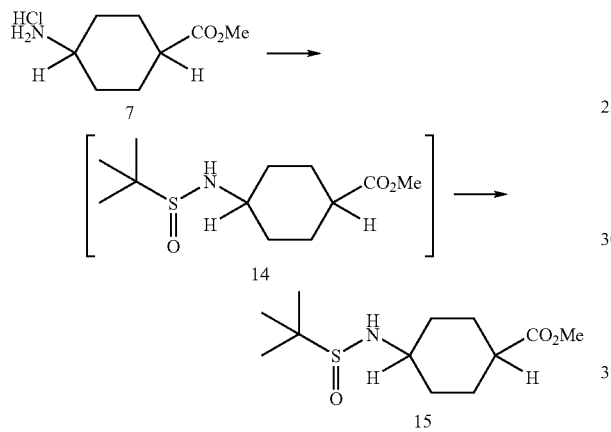

After the mixture of 28.4 kg of DMF, 8.4 kg of butylsulfinyl chloride and 10.6 kg of Compound (7) was cooled to −9 DC, 12.7 kg of triethylamine was added dropwise at −9° C. to 2° C. The mixture was stirred for 60 minutes at 0° C. to 6° C. and 21.2 kg of water was added. To the mixture was added dropwise 3.5% aqueous solution of hydrochloric acid at 4° C. to 8° C.

A solution of 2.00 kg of ammonium heptamolybdate tetrahydrate in 10.40 kg of water was added to the mixture and heated to 40° C. To the mixture was added dropwise 8.0 kg of 35% hydrogen peroxide solution at 40° C. to 45° C. and stirred for 130 minutes at 40° C. to 44° C. The reaction mixture was cooled to 22° C. and poured into the mixture of 7.4 kg of sodium chloride, 7.4 kg of sodium sulfide, and 99.6 kg of water to remove remained peroxide. The mixture was stirred for 60 minutes at 25° C. to 30° C. and filtered with Buechner funnel. The filtrate was washed with 13.8 kg of water three times. After wet crystals were separated, 136.9 kg of ethyl acetate and 30.4 kg of water were added and the mixture was heated to 39° C. After the crystals were dissolved, aqueous layer was removed and ethyl acetate was concentrated to about 30 kg by removing ethyl acetate. To the mixture was added 106.3 kg of cyclohexane and the mixture was concentrated to about 90 kg and stirred for 90 minutes at 26° C. to 28° C. After the appeared crystals were separated, they were washed with 11.8 kg of cyclohexane twice and dried under reduced pressure at 50° C. to obtain 12.58 kg of Compound (15) (82.9% from aminomethyl ester hydrochloride (4)).

Example 8

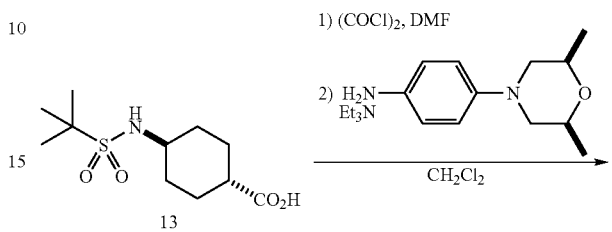

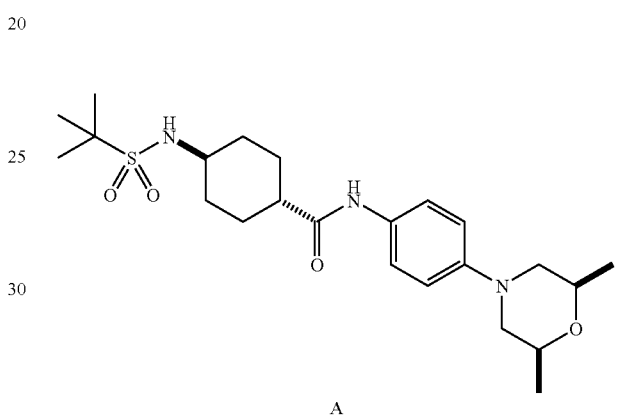

Starting material carboxylic acid (13) (5.86 g, 22.3 mmol) was dissolved in 88 ml of dichloromethane at room temperature, and oxalyl chloride (2.34 ml, 26.7 mmol) and catalytic amount of DMF were added to the mixture with ice-cooling. The mixture was stirred for 1 hour at room temperature and the solvent was removed under reduced pressure. After 115 ml of dichloromethane was added, substituted aniline (5.05 g, 24.5 mmol) and triethylamine (4.65 ml, 33.4 mmol) were added. The mixture was stirred for 2.5 hours at room temperature, and ice water was poured into the mixture. The mixture was extracted with chloroform, and the organic layer was washed with water and dried over a hydrous magnesium sulfate. After the solvent was removed under reduced pressure, ethyl acetate and hexane were added to the residue and appeared crystals were collected by filtration to obtain Amide Compound A (7.00 g, 70% yield).

Example 9

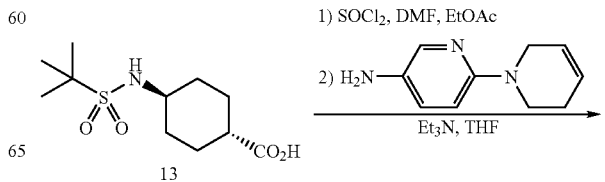

-continued

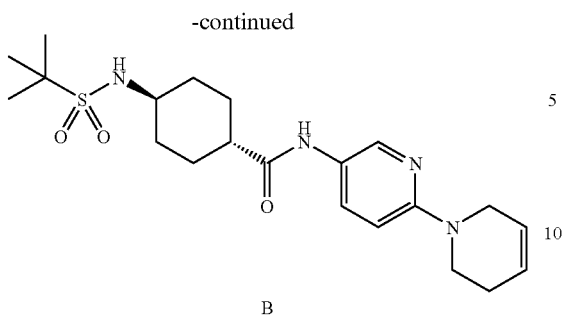

B

Starting material Carboxylic acid (13) (2.00 g, 7.59 mmol) was dissolved in 20 ml of ethyl acetate at room temperature, and thionyl chloride (0.61 ml, 8.36 mmol) and catalytic amount of DMF were added to the mixture. After the mixture was stirred for 1.5 hours at room temperature, the solvent was removed under reduced pressure. After 20 ml of tetrahydrofuran was added to the residue, substituted aniline (1.33 g, 7.59 mmol) and triethylamine (3.18 ml, 22.8 mmol) were added. The mixture was stirred for 3 hours at room temperature, and 40 ml of water was poured into the mixture. The mixture was ice-cooled and appeared crystals were collected by filtration to obtain Amide Compound B (2.60 g, 81.4%).

$^1$H NMR (DMSO-$d_6$): 1.26 (s, 9H), 1.40 (m, 4H), 1.83 (d, J=11.7 Hz, 2H), 1.95 (d, J=9.7 Hz, 2H), 2.16 (m, 3H), 3.04 (m, 1H), 3.60 (t, J=5.6 Hz, 2H), 3.83 (t, J=2.5 Hz, 2H), 5.83 (m, 2H), 6.77 (dd, J=9.1 Hz, 16.9 Hz, 2H), 7.75 (dd, J=2.7 Hz, 9.1 Hz, 1H), 8.26 (d, J=2.7 Hz, 1H), 9.63 (s, 1H)

Example 10

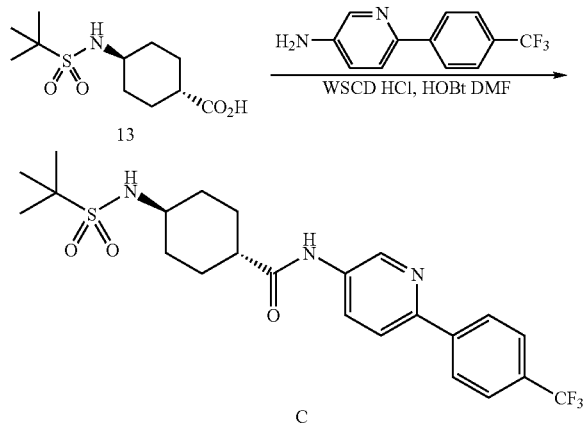

C

Starting material carboxylic acid (13) (316 mg, 1.20 mmol) was dissolved in 5 ml of DMF at room temperature, and substituted aniline (286 mg, 1.20 mmol), N-hydroxybenzotriazole (195 mg, 1.44 mmol) and 1-ethyl-3-(3'-dimethylaminopropyl)carbodiimide hydrochloride (276 mg, 1.44 mmol) were added to the mixture. After the mixture was stirred for 14 hours at room temperature, water was poured into the mixture and the mixture was extracted with chloroform twice, The combined organic layer was washed with brine and dried over sodium sulfate. After the solvent was removed under reduced pressure, methanol was added to the residue and appeared crystals were collected by filtrate to obtain Amide Compound C (195 mg, 33.6%).

$^1$H NMR (DMSO-$d_6$): 1.27 (s, 9H), 1.43 (m, 4H), 1.88 (d, J=12.6 Hz, 2H), 1.98 (d, J=11.7 Hz, 2H), 2.29 (m, 1H), 3.07 (m, 1H), 6.81 (d, J=8.4 Hz, 1H), 7.76 (d, J=8.7 Hz, 2H), 8.13 (m, 3H), 8.23 (dd, J=2.3 Hz, 8.6 Hz, 1H), 8.99 (s, 1H), 10.07 (s, 1H)

Example 11

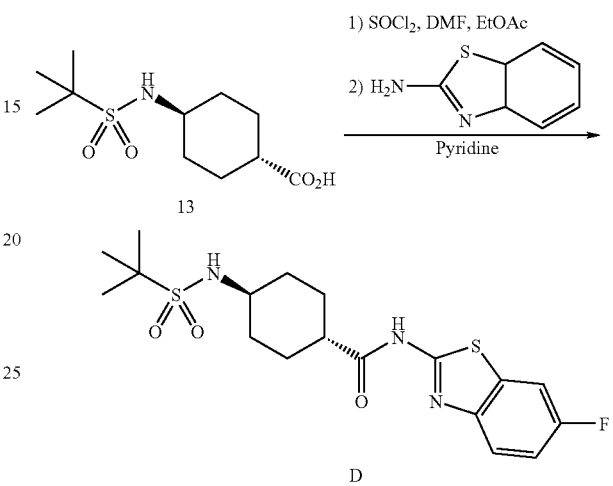

D

Starting material Carboxylic acid (13) (1.05 g, 4.00 mmol) was dissolved in 30 ml of ethyl acetate at room temperature, and thionyl chloride (4.5 ml, 61.7 mmol) and catalytic amount of DMF were added to the mixture. After the mixture was stirred for 1 hour at room temperature, the solvent was removed under reduced pressure. Substituted aniline (664.2 mg, 3.95 mmol) and 10 ml of pyridine were added to the residue. The mixture was stirred for 4 hours at 60° C., and 50 ml of water was poured into the mixture. The mixture was stirred with ice-cooling and the appeared crystals were collected by filtrate to obtain Amide Compound D (2.23 g, 55.5%).

$^1$H NMR (DMSO-$d_6$): 1.27 (s, 9H), 1.39 (m, 3H), 1.95 (c, 4H), 2.45 (t, J=11.6 Hz, 1H), 3.10 (m, 1H), 3.34 (m, 1H), 6.83 (d, J=8.6 Hz, 1H), 7.28 (td, J=2.7 Hz, 9.1 Hz, 1H), 7.74 (dd, J=4.8 Hz, 8.8 Hz, 1H), 7.88 (dd, J=2.5 Hz, 8.6 Hz, 1H), 12.31 (s, 1H)

Example 12

The following Compounds (XII) are synthesized using NH$_2$—Z (XI-1) as a starting material in the similar manner to Examples 8 to 11.

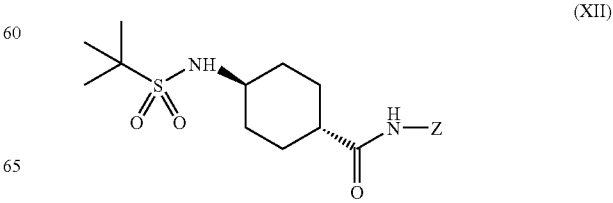

(XII)

The invention claimed is:

1. A process for the preparation of a compound of the formula:

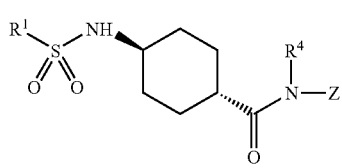

(XII)

wherein $R^1$ is lower alkyl, $R^4$ is hydrogen or lower alkyl, and Z is optionally substituted lower alkyl, optionally substituted lower alkenyl, optionally substituted amino, optionally substituted lower alkoxy, optionally substituted carbocyclyl or optionally substituted heterocyclyl, comprising:

a) reacting a compound of the formula (IV)

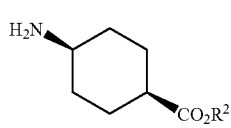

(IV)

wherein $R^2$ is lower alkyl with a compound of the formula (VI)

$$R^3\text{—CHO} \qquad (VI)$$

wherein $R^3$ is optionally substituted phenyl to obtain a compound (VII),

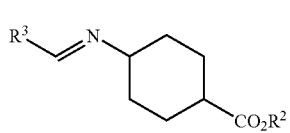

(VII)

wherein $R^2$ and $R^3$ are defined as above, b) reacting (VII) with a base in an organic solvent to obtain the compound (VIII)

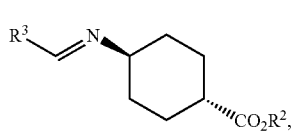

(VIII)

c) hydrolyzing the compound (VIII) to obtain compound (IX)

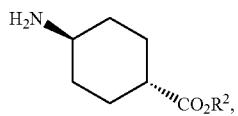

(IX)

INDUSTRIAL APPLICABILITY

Trans-4-amino-1-cyclohexancarboxylic acid derivatives which are useful as an intermediate of a medicament can be efficiently produced by the processes of the present invention. The present invention also provides intermediates which are used for the processes of the present invention.

d) reacting compound (IX):

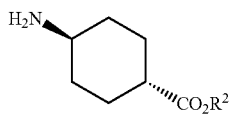
(IX)

wherein R2 is lower alkyl with a compound of the formula:

(V)

wherein R1 is lower alkyl to obtain a compound of the formula:

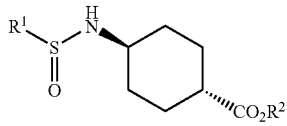
(X)

wherein R1 and R2 are each independently lower alkyl,
e) oxidizing compound (X) to obtain compound (I)

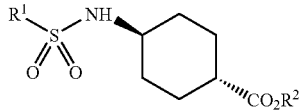
(I)

wherein R1 and R2 are each independently lower alkyl,
f) hydrolyzing Compound (I) to obtain Compound (I')

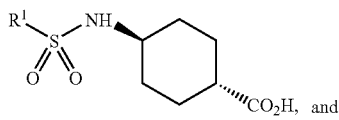
(I')

and g) reacting Compound (I')

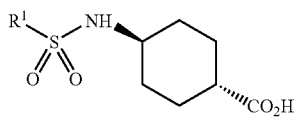
(I')

with a compound of the formula:

 (XI)

wherein $R^4$ and Z are the same as defined above, to obtain compound (XII).

2. A process for the preparation of a compound of the formula:

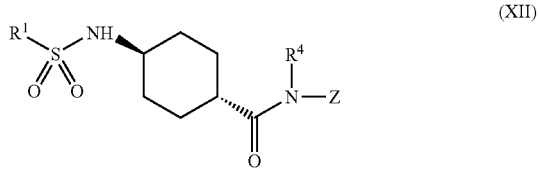
(XII)

wherein $R^1$ is lower alkyl, $R^4$ is hydrogen or lower alkyl, and Z is optionally substituted lower alkyl, optionally substituted lower alkenyl, optionally substituted amino, optionally substituted lower alkoxy, optionally substituted carbocyclyl or optionally substituted heterocyclyl, comprising:

a) reacting a compound of the formula:

(IV)

wherein $R^2$ is lower alkyl, with a compound of the formula:

(V)

wherein $R^1$ is lower alkyl, to obtain a compound of the formula:

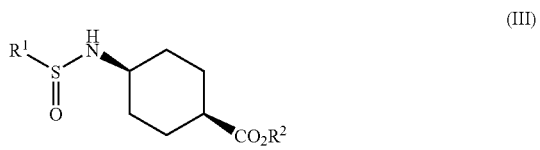
(III)

wherein each symbol is the same as defined above, b) oxidizing Compound (III) to obtain

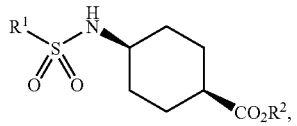
(II)

c) reacting a compound of the formula (II) with a base in an aprotic solvent to obtain compound (I)

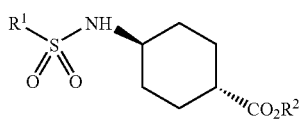
(I)

wherein R1 and R2 are each independently lower alkyl, f) hydrolyzing Compound (I) to obtain Compound (I')

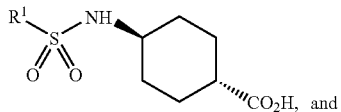
(I')

and g) reacting Compound (I')

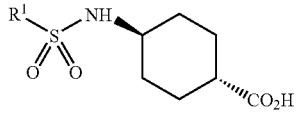
(I')

with a compound of the formula:

R⁴NH—Z (XI)

wherein $R^4$ and Z are the same as defined above, to obtain compound (XII).

3. The process as claimed in claim 2 wherein $R^1$ is t-butyl and $R^2$ is methyl.

4. The process as claimed in claim 2 wherein the base is selected from a group of an alkaline metal lower alkoxide, and alkaline metal hydride and an alkaline metal amide.

5. The process as claimed in claim 4 wherein the base is an alkaline metal lower alkoxide.

6. The process as claimed in claim 2 further comprising recrystallizing Compound (I) in an aprotic solvent.

7. The process as claimed in claim 6 wherein the aprotic solvent is a nonpolar aprotic solvent.

8. The process as claimed in claim 7 wherein the aprotic solvent is toluene.

9. The process as claimed in claim 2 comprising hydrolyzing compound (I) which is not isolated from a reaction solution.

10. The process according to claim 1 wherein $R^3$ is nitrophenyl.

* * * * *